US007981878B2

(12) United States Patent
Hubmann et al.

(10) Patent No.: US 7,981,878 B2
(45) Date of Patent: Jul. 19, 2011

(54) TUMOR TREATMENT WITH GLIOTOXIN DERIVATIVES

(75) Inventors: Rainer Hubmann, Vienna (AT); Wolfgang Sieghart, Vienna (AT)

(73) Assignee: Medizinische Universitat Wien, Vienna (AT)

( * ) Notice: Subject to any disclaimer, the term of this patent is extended or adjusted under 35 U.S.C. 154(b) by 157 days.

(21) Appl. No.: 11/993,804

(22) PCT Filed: Jun. 21, 2006

(86) PCT No.: PCT/AT2006/000253
§ 371 (c)(1),
(2), (4) Date: Dec. 21, 2007

(87) PCT Pub. No.: WO2006/135949
PCT Pub. Date: Dec. 28, 2006

(65) Prior Publication Data
US 2009/0029974 A1 Jan. 29, 2009

(30) Foreign Application Priority Data
Jun. 21, 2005 (AT) .............................. A 1044/2005

(51) Int. Cl.
*A01N 43/00* (2006.01)
*A61K 31/33* (2006.01)
*A61K 31/54* (2006.01)
(52) U.S. Cl. .................................. 514/183; 514/222.8
(58) Field of Classification Search .................. None
See application file for complete search history.

(56) References Cited

U.S. PATENT DOCUMENTS

| 2004/0101847 | A1* | 5/2004 | Freier et al. ............ 435/6 |
| 2004/1001847 | | 5/2004 | Freier et al. ............ 435/6 |
| 2004/0137569 | A1* | 7/2004 | Chan et al. ........... 435/69.1 |

FOREIGN PATENT DOCUMENTS

| EP | 0 163 475 | 12/1985 |
| EP | 0 926 242 | 6/1999 |
| JP | 61-277617 | 12/1986 |
| JP | 6220065 | 8/1994 |
| JP | 7227293 | 8/1995 |
| WO | WO 92/10198 | 6/1992 |
| WO | WO 2004/019921 | 3/2004 |

OTHER PUBLICATIONS

Tompsett et al. Tuberculostatic activity of blood and urine from animals given gliotoxin. Cornell Medical Center, New York. Feb. 6, 1950.*
Karon & Klyce. Effect of inhibition of inflammatory mediators on trauma-induced stromal edema. Investigative Ophthalmology & Visual Science, Jun. 2003, vol. 4, No. 6, pp. 2507-2510.*
Vigushin et al. Gliotoxin is a dual inhibitor of farnesyltransferase and geranylgeranyltransferase I with antitumor activity against breast cancer in vivo. Medical Oncology, vol. 21, No. 1, 21-30, 2004.*
Tiwari et al. Among circulating hematopoietic cells, B-CLL uniquely expresses functional EPAC1, but EPAC1-mediated Rap1 activation does not account for PDE4 inhibitor-induced apoptosis. Blood, 2004, 103: 2661-2667.*
Marzo et al. Farnesyltransferase inhibitor BMS-214662 induces apoptosis in B-cell chronic lymphocytic leukemia cells. Leukemia, 2004, 18, 1599-1604.*
Sutton et al. Evidence that gliotoxin enhances lymphocyte activation and induces apoptosis by effects on cyclic AMP levels. Biochemical Pharmacology, vol. 50, No. 12, pp. 2009-2014,1995.*
Gaiger et al. Novel molecular diagnostic and therapeutic targets in chronic lymphocytic leukaemia. European Journal of Clinical Investigation, 34 (Suppl. 2), 25-30, 2004.*
Cuevas et al., "Meningioma transcript profiles reveal deregulated Notch signaling pathway," *Cancer Res.*, 65:5070-5075, 2005.
Fan et al., "Notch1 and notch2 have opposite effects on embryonal brain tumor growth," *Cancer Res.*, 64:7787-7793, 2004.
Gardiner et al., "The epipolythiodioxopiperazine (ETP) class of fungal toxins: distribution, mode of action, functions and biosynthesis," *Microbiology*, 151:1021-1032, 2005.
Garnis et al., "Involvement of multiple developmental genes on chromosome 1p in lung tumorigenesis," *Hum. Mol. Gen.*, 14:475-82, 2004.
Hoek et al., "Expression profiling reveals novel pathways in the transformation of melanocytes to melanomas," *Cancer Res.*, 64:5270-82, 2004.
Hubmann et al., "Involvement of PKC-delta in the regulation of Notch2 ni B-CLL," *Blood*, 106(11):Abstract 4990, 2005.
Hubmann et al., "Notch2 is involved in the overexpression of CD23 in B-cell chronic lymphocytic leukemia," *Blood*, 99:3742-7, 2002.
Hurne et al., "Inactivation of rabbit muscle creatine kinase by reversible formation of an internal disulfide bond induced by the fungal toxin gliotoxin," *JBC*, 275:25202-6, 2000.
Jansen et al., "bcl-2 antisense therapy chemosensitizes human melanoma in SCID mice," *Nat. Med.*, 4:232-234, 1998.
Jehn et al., "Cutting edge: protective effects of notch-1 on TCR-induced apoptosis," *JI*, 162:635-8, 1999.
Jundt et al., "Novel gamma-secretase inhibitor DAPT blocks activated notch signaling and controls tumor cell growth in Hodgkin and anaplastic large cell lymphoma," *Blood*, 100(11):Abstract 594, 2002.
Knowles et al., "Human hepatocellular carcinoma cell lines secrete the major plasma proteins and hepatitis B surface antigen," *Science*, 209:497-499, 1980.
Kweon et al., "Gliotoxin-mediated apoptosis of activated human hepatic stellate cells,"*J. Hepato.*, 39:38-42, 2003.
Lauring and Overbaugh, "Evidence that an IRES within the Notch2 coding region can direct expression of a nuclear form of the protein," *Mol. Cell*, 6:939-45, 2000.
Lee et al., "Anti-angiogenic activities of gliotoxin and its methylthioderivative, fungal metabolites," *Arch. Pharm. Res.*, 24:397-401, 2001.

*Primary Examiner* — Brandon J Fetterolf
*Assistant Examiner* — Anna Pagonakis
(74) *Attorney, Agent, or Firm* — Fulbright & Jaworski LLP

(57) ABSTRACT

The present invention describes the use of Notch2 inhibitors for producing a medicament for the treatment of tumours, which tumours are characterized by ligand-independent Notch2 fragments.

17 Claims, 7 Drawing Sheets

OTHER PUBLICATIONS

Figure 1:
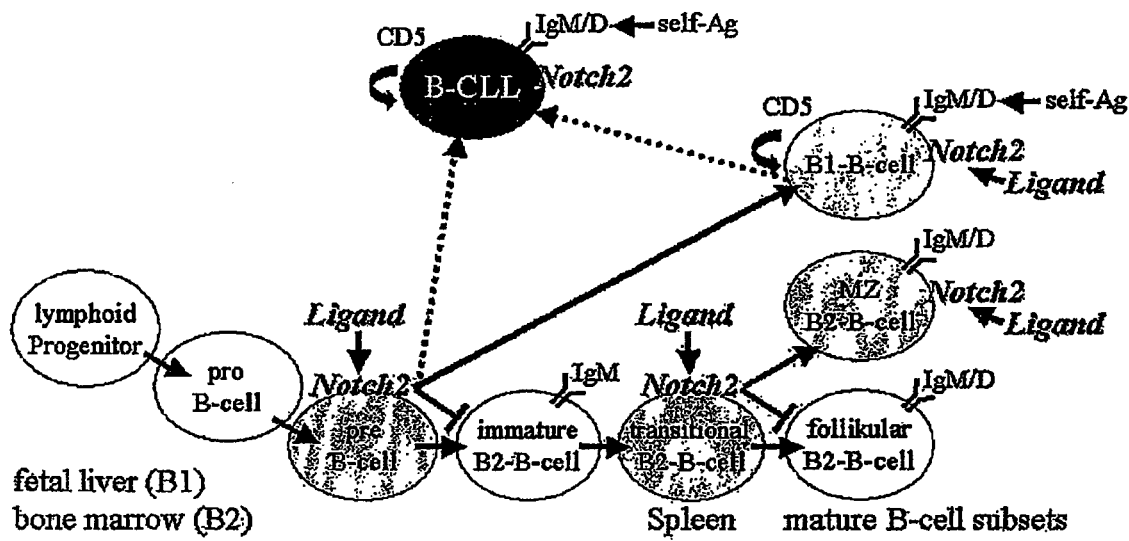

Lee et al., "Notch 2-positive progenitors with the intrinsic ability to give rise to pancreatic ductal cells," *Lab. Invest.*, 85:1003-12, 2005.

Lehmann et al., "MUC18, a marker of tumor progression in human melanoma, shows sequence similarity to the neural cell adhesion molecules of the immunoglobulin superfamily," *Proc. Natl. Acad. Sci. USA*, 86:9891-9895, 1989.

Leong and Karsan, "Recent insights into the role of Notch signaling in tumorigenesis," *Blood*, 107:2223-33, 2006.

Lewis et al., "Detection of gliotoxin in experimental and human aspergillosis," *Infect. and Immun.*, 73:635-7, 2005.

Lieber et al., "Establishment of a continuous tumor-cell line (panc-1) from a human carcinoma of the exocrine pancreas," *Int. J. Cancer*, 15:741-747, 1975.

Lin et al., "Conversion of Bcl-2 from protector to killer by interaction with nuclear orphan receptor Nur77/TR3," *Cell*, 116:527-40, 2004.

Maillard et al., "Mastermind critically regulates Notch-mediated lymphoid cell fate decisions," *Blood*, 104:1696-1702, 2004.

Martin et al., "Quantitative proteomic analysis of proteins released by neoplastic prostate epithelium," *Cancer Res.*, 64:347-55, 2004.

Massi et al., "Evidence for differential expression of Notch receptors and their ligands in melanocytic nevi and cutaneous malignant melanoma," *Modern Pathology*, 19:246-254, 2006.

Miele, "Notch signaling," *Clin. Cancer Res.*, 12:1074-9, 2006.

Müllbacher et al., "Selective resistance of bone marrow-derived hemopoietic progenitor cells to gliotoxin," *PNAS*, 84:3822-5, 1987.

Nickoloff et al., "Notch signaling as a therapeutic target in cancer: a new approach to the development of cell fate modifying agents," *Oncogene*, 22:6598-6608, 2003.

Orr et al., "Mechanism of action of the antifibrogenic compound gliotoxin in rat liver cells," *Hepatology*, 40:232, 2004.

Paris et al., "Inhibition of angiogenesis and tumor growth by β and γ-secretase inhibitors," *European Journal of Pharmacology*, 514:1-15, 2005.

Park et al., "Characterization of cell lines established from human hepatocellular carcinoma," *Int. J. Cancer*, 62:276-282, 1995.

Parr et al., "The possible correlation of Notch-1 and Notch-2 with clinical outcome and tumour clinicopathological parameters in human breast cancer," *Int. J. Mol. Med.*, 14:779-786, 2004.

Radtke and Raj, "The role of Notch in tumorigenesis: oncogene or tumour suppressor?," *Nat. Rev. Cancer*, 3:756-67, 2003.

Santagata et al., "JAGGED1 expression is associated with prostate cancer metastasis and recurrence," *Cancer Res.*, 64:6854-6857, 2004.

Schwarzmeier et al., "Regulation of CD23 expression by Notch2 in B-cell chronic lymphocytic leukemia," *Leuk. Lymphoma*, 46:157-165, 2005.

Sutton et al., "In vivo immunosuppressive activity of gliotoxin, a metabolite produced by human pathogenic fungi," *Infect. and Immun.*, 62:1192-8, 1994.

Vigushin et al., "Gliotoxin is a dual inhibitor of farnesyltransferase and geranylgeranyltransferase I with antitumor activity against breast cancer in vivo," *Med. Oncol.*, 21:21-30, 2004.

Yunis et al., "Human pancreatic carcinoma (MIA PaCa-2) in continuous culture: sensitivity to asparaginase," *Int. J. Cancer*, 19:128-135, 1977.

Zhang et al., "Notch signaling pathway contributes to osteosarcoma growth, tumorigenesis and metastasis," *AACR Meeting Abstracts*, 2006.

* cited by examiner

TUMOR TREATMENT WITH GLIOTOXIN DERIVATIVES

This application is a national phase application under 35 U.S.C. §371 of International Application No. PCT/AT2006/000253 filed 21 Jun. 2006, which claims priority to Austrian Patent Application No. A 1044/2005 filed 21 Jun. 2005. The entire text of each of the above-referenced disclosures is specifically incorporated herein by reference without disclaimer.

The present invention relates to the treatment of tumours.

Chronic lymphatic leukaemia of the B-cell type (B-CLL) is the most frequent form of leukaemia in the Western hemisphere. The leukocyte number in bone marrow, blood, lymph tissue and other organs is clearly increased, the lymphocyte content contained therein may be up to 95%. In most cases, older people starting from their $50^{th}$ year of life are affected. The disease is characterised by a gradual accumulation of a CD5/CD19/CD23 positive (mature) B-cell clone which is based on a defect in programmed cell death (apoptosis). The origin of the B-CLL seems to be auto-reactive, CD5-positive B1-B cells which are formed during the embryogenesis in the fetal liver, colonise certain areas in secondary lymphoid organs and in the peritoneum and are characterised by their self-renewing capacity. In the early ontogenesis, B1-B cells play an important part for the innate immunity, yet they are successively replaced by T-helper-cell-dependent B2-B memory cells. The homeostasis of these cells is regulated by the B-cell receptor (BCR) which has affinity to certain self-antigens. If a CD5+B1 B-cell leaves its compartment, the activation-induced cell death (AICD) is triggered by the interaction with these self-antigens, thereby preventing an uncontrolled expansion of these autoreactive B-cells.

Gliotoxin ([3R-(3α,5aβ,6β,10aα)]-2,3,5a,6-tetrahydro-6-hydroxy-3-(hydroxymethyl)-2-methyl-10H-3,10a-epi-dithiopyrazino[1,2-a]indol-1,4-dion) is a secondary fungus metabolite, which is formed by *Aspergillus fumigatus, A. flavus, A. niger* and *A. terreus*. This substance belongs to the epipolythiodioxopiperazines, which are most likely to play a central part in the mortality during systemic Aspergilloses ($LD_{50}$ in mice and rats: 25-50 mg/kg; Taylor et al., Microb. Toxins 7:337; 1971).

The effects of gliotoxin are diverse and include the inhibition of viral reverse transcriptases, the binding to alcohol dehydrogenases, the inhibition of transcription factor NF-κB—the modulation of the calcium influence in cells and toxic effects on erythrocytes (Gardiner et al., Microbiology 151: 1021-1032, 2005). The molecular effects include the catalytic opening and closing of cysteine bridges, the binding to cysteine and thiol residues, and the formation of reactive oxygen species via a redox circulation. In cultures from animal cells, gliotoxin exhibits an apoptotic effect at low concentrations. At concentrations of more than 10 μM, the effect changes towards necrosis, with a complete necrosis of the cell cultures starting from concentration of 50 μM. Even though formerly thought to be active as a proteosome inhibitor, this view is no longer held, since the very high gliotoxin concentration required therefore suggests an unspecific effect.

At low doses, gliotoxin exhibits a potent immunosuppressivity. In mice, a single administration of 100 μg of gliotoxin leads to a complete loss of B1 B-cells (LPS responder), while the T-cell functions are only shortly influenced. In mouse models, the side effects of a gliotoxin treatment are apoptosis of mature macrophages, B-cells of the spleen (splenocytes), thymocytes and of cells of the mesenterial lymph nodes (Sutton et al., Infect. and Immun. 62: 1192; 1994), as well as endothelial cells (HUVEC) (Lee, H. J. Arch Pharm Res 24 (5) (2001): 397-401, abstract).

Hematopoietic precursor cells are not affected by these side effects, which might explain the relative rapid regeneration of the immune system after a single gliotoxin treatment (Müllbacher et al., PNAS 84: 3822; 1987).

Furthermore, in systemic *Aspergillus* infections, the mycotoxin gliotoxin appears to specifically circumvent the innate immunity by selectively inhibiting the splenocytes.

Gliotoxin is a known inhibitor of the transcription factor NfκB and of the Farnesyl transferase (Hurne et al., JBC 275: 25202; 2000). As a possible mechanism of action, a reversible reaction of gliotoxin with exposed thiol groups of cysteines has been proposed, whereby sulphur bridges are temporarily formed in these proteins.

Gliotoxin has already been suggested to be used as an immunosuppressive agent (Sutton et al., Infect. Immun. 62 (4): 1192; 1994) as an antifibrotic agent (Orr et al., Hepatology 40(1): 232; 2004) and as an anti-tumour agent against breast cancer (Vigushin et al., Med. Oncol. 21(1): 21; 2004). In other publications it was found that gliotoxin promotes cancer during aspergillosis (Lewis et al., Inf. and Immun. 73(1): 635 (2005)) through its immunosuppressive effects.

In EP 163475, gliotoxin-like substances and their application for preventing rejection reactions after transplantations have been described.

In JP 61277617, gliotoxin is claimed as an inhibitor of platelet aggregation.

In WO 2004/19921 and in Kweon et al. (J. Hepatol. 39(1): 38; 2003), the use of gliotoxin as an apoptose-triggering agent for hepatic stellate cells in liver fibrosis has been described.

In JP 6220065, gliotoxin derivatives have been mentioned as cell growth inhibitors.

It is an objective of the present invention to provide efficient and nevertheless well-tolerable anti-tumour agents which specifically interfere with the process of tumour formation.

The present invention includes the use of Notch2-inhibitors for producing a medicament for the treatment of tumours which are characterised by ligand-independent Notch2 fragments. The term "tumour, characterised by ligand-independent Notch2 fragments" is also called "Notch2-associated tumour. Abnormal Notch2 variants in tumour cells have been identified as a central factor promoting tumourgenesis. Application of specific Notch2 inhibitors resulted in massive induction of apoptosis in Notch2 associated tumours. Therefore, a specific anti-tumour treatment is enabled. In particular, the function of the Notch2 protein, preferably of the intracellular component of the Notch2 protein ($N2^{IC}$), is inhibited. This activity of the Notch2 inhibitors of the present invention proves itself to be apoptotic active, selective on Notch2-associated carcinogenic cells.

Notch receptors act as intracellular junctions in binary differentiation processes. Depending on the cellular context, Notch signals modulate the apoptosis, proliferation and differentiation of cells. The spleen is preferably colonised by Notch2-expressing B1-B cells and the closely related Notch2-expressing marginal zone (MZ) B2-B cells (cf. FIG. 1).

In B-CLL, a deregulation of the Notch2 oncogene causes the blocking of the AICD ("activation induced cell death"), which normally ensures homeostasis of these autoreactive B1-B cells. The AICD is controlled via the orphan steroid receptor NR4A1 (also known as nur77 or TR3), a factor which belongs to the immediate early genes induced by mitogenic signals. An apoptotic B-cell receptor signal leads to the expression of NR4A1 which, by interaction with BCL2 in mitochondria causes the induction of the cytochrome-C-dependent apoptosis (Lin et al., Cell 116: 527; 2004). Activated Notch receptors bind to NR4A1 in the cell nucleus thus blocking its function in the cytosol (Jehn et al., JI 162: 635; 1999).

With the help of reverse genetics it has been possible to identify Notch2 as that transcription factor which is responsible for the overexpression of CD23 in the B-CLL (Hubmann et al., BLOOD 99: 3742; 2002 and Schwarzmeier et al., Leukemia & Lymphoma 46: 157; 2005). Notch2 is a transmembrane receptor, which is activated by neighbouring cells by defined ligands (Jagged/Delta). This activation causes γ-secretase-mediated cleavage of the intracellular portion of Notch2 ($N2^{IC}$) which translocates into the nucleus and thereby controls the expression of CBF1-regulated target genes, such as Hes, p21, CyclinD1, Erbb2, NfκB2 and CD23. In combination with the coactivator MAML, $N2^{IC}$ converts the repressor protein CSL into an activator of transcription.

Peripheral B-CLL cells have an increased Notch2 activity, suggesting a deregulation of this signal transduction pathway. Due to gene defects, the expression of truncated, ligand-independent Notch2 forms occurs which have been identified as tumour-initiating oncogenes in model systems (Nickoloff et al., Oncogene 22: 6598; 2003 and Radke et al., Nat. Rev. Cancer 3: 756; 2003). Depending on the cellular context, a deregulation of Notch2 oncogenes leads to an immortalisation and a differentiation arrest of cells. Moreover, the oncogenic function of Notch receptors offers a protection against diverse pro-apoptotic signals. Notch inhibits JIP1 dependent activation of the c-Jun N-terminal kinase (JNK), suppresses p53 by a mdm2 dependent pathway, induces phosphatidylinositol 3-kinase (PI3K) and NFκB signaling, and interferes with the apoptotic function of the orphan steroid receptor NR4A1 a mediator of T-cell and B-cell receptor induced cell death (AICD for activation induced cell death) (Radtke et al., Nat. Rev. in Cancer 3: 756; 2003; Miele, Clin. Ca. Res 12 (4): 1074; 2006; Leong et al., Blood 107 (6:2223; 2006).

In B-cell precursors, over expression of a constitutively active Notch2 protein leads to selective development of B1-B cells, and in the spleen it leads to the selective development of marginal zone (MZ) B2-B cells. Deregulation of Notch2 also plays a central part in the B-CLL pathogenesis in that it immortalises the malignant clone and protects it from the peripheral negative selection (Schwarzmeier et al., Leukemia & Lymphoma 46: 157; 2005). In particular, $N2^{IC}$ blocks the apoptotic function of steroid receptor NR4A1.

Within the scope of the present invention it has been found that the activity of Notch2 does not only correlate with the viability of B-CLL cells, but also that Notch2 rescues B-cells from B-cell-receptor-mediated apoptosis (AICD), a mechanism known to prevent the uncontrolled expansion of self-reactive B1-B cells (B1-B cells obtain their physiological Notch2 signal in certain compartments). Furthermore, investigations have shown that B-CLL cells express a ligand-independent form of Notch2 (cf. Example 4).

These ligand-independent Notch2 fragments (also termed aberrant Notch2 fragments of signal- or ligand-independent Notch2 fragments or Notch2$^{IC}$) are characterised by truncated forms of Notch2 starting from a start codon two amino acids downstream of the γ-secretase cleavage site (S3 site) (Lauring et al. Mol. Cell 6 (4): 939; 2000). These Notch2 fragments lack the trans-membrane domain and the γ-secretase cleavage site and, thus, are resistant to state of the art Notch inhibitors (ie. γ-secretase inhibitors) like DAPT and Compound E (cf. FIG. 6A). The Notch2 Inhibitor according to the present invention is an inhibitor of the ligand-independent Notch2 fragments—like gliotoxin and its derivatives—and preferably a specific (and e.g. non-specific for normal Notch2) inhibitor thereof.

Figure 7:
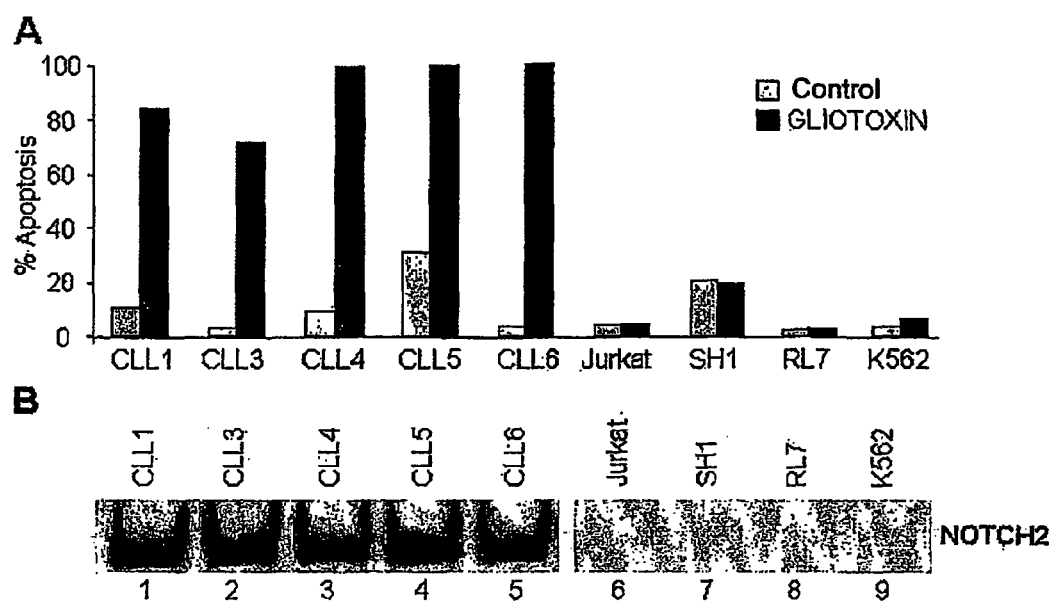

Even though acetylgliotoxin, gliotoxin and aromatic gliotoxin derivatives have been mentioned in the context of methods for the treatment of tumours (EP 926 242 A1), wherein it has been indicated that acetylgliotoxin was effective against human leukaemia cells (cell lines K 562, U 937 (monocyte leukaemia): Dainippon Seiyaku), human carcinoma cells of the intestines (cell lines HCT-15, HCT-116, SW946; Dainippon Seiyaku), human lung cancer cells (cell lines LX-1: Biseibutsu Kagaku Kenyu-sho) mouse leukaemia cells (cell line P 388: Dainippon Seiyaku) and mouse carcinoma cells of the intestines (cell lines colon-26: Gan Kenkyu-kai, Gan Kenkyu-sho), the apoptotic activity of gliotoxin and its derivatives could not be proven in other cancer cell lines, among them leukaemias (cf. i.a. FIGS. 7, 8A, infra), so that a general efficacy of gliotoxin as an anti-tumour agent is not given. For some of these cell lines the necessary gliotoxin concentration was so high to indicate unspecific cellular cytotoxicity. Gliotoxin was even mentioned to be a cancer promoting agent in other publications since gliotoxin presence related to opportunistic *aspergillus* infections was abundantly found in cancer patients (Lewis et al., Inf. and Immun. 73(1): 635 (2005)). The anti-carcinogenic activity according to the present invention was a surprising exception, contrary to the rule. For instance, it could be demonstrated that the Notch2 inhibitor gliotoxin is not in general effective against leukaemias, and against solid tumours, respectively.

The present invention provides the means and indications to provide a therapy of Notch2-associated tumours and cancers. Because the underlying mechanism has been identified any inhibitor of the ligand independent Notch2 fragment can be used for a therapeutic treatment. The US 2004/01001847 A1, for example provides Notch2-inhibitors on nucleotide basis, specifically anti-sense inhibitor nucleotides, which can be used in effective amounts (within the therapeutic concentration window, below a counter indicative toxic concentration) for the medicament (and the treatment) of the present invention.

A preferred embodiment of the present invention is a use, characterised by the fact that the Notch2 inhibitor (in the context of the present invention an inhibitor of the ligand independent Notch2 fragment) is gliotoxin. Gliotoxin is a known mycotoxin and, i.a., is also used as an active agent for diverse applications. Gliotoxin can be prepared by a whole series of different methods which are sufficiently known from the prior art. One example thereof is disclosed in JP 7227293, in which a method for the gliotoxin production by viruses is described.

Preferably, the Notch2 inhibitors, or gliotoxin, respectively, are administered in a pharmaceutically administrable form (in effective amounts), which may additionally contain diverse salts as stabilising buffer, or in which the inhibitor is, e.g., present as an ester which can be cleaved in vivo for a better uptake/pharmacodynamics. Via gliotoxin, Notch2—being an adapter protein—could be influenced in its natural function as a linkage protein in the Notch2-regulated transcription factor complex. The actual cytotoxic moiety is a reduced form of gliotoxin. For this metabolite in turn is not possible to leave the cell and becomes entrapped. Cells with a high metabolism, like cancer cells, have an increased uptake of gliotoxin and therefore reduced gliotoxin is concentrated in the primary targets of the treatment. Gliotoxin is only released from the cells upon cell death and can then develop new toxic effects for the cancer cells in the vicinity (Redox-cycling).

A further use of the present invention is characterised in that the Notch2 inhibitor is a gliotoxin derivative, preferably selected from the group consisting of acetylgliotoxin, 6-$C_{1-3}$-alkoxygliotoxin, 6-$C_{2-3}$-acyloxy-gliotoxin, 6-dihydro-gliotoxin, 6-dihydroxy-gliotoxin, 6-[(methoxycarbonyl) methoxy]-gliotoxin and 6-cyanomethoxy-gliotoxin, and the salts thereof. These gliotoxin derivatives can easily be prepared from gliotoxin by any means known from the prior art. For instance, EP 926 242 A1 describes diverse chemical synthesis pathways for their production. In an accordingly simple manner, gliotoxin ([3R-(3α,5aβ,6β,10aα)]-2,3,5a,6-tetrahydro-6-hydroxy-3-(hydroxymethyl)-2-methyl-10H-3,10a-epi-dithiopyrazino[1,2a]indol-1,4-dion) can be chemically modified at its 6-position, wherein the disulfide group preferably is protected by the transitional binding of a protective group.

Further preferred gliotoxin derivatives to be used according to the present invention are Notch2 inhibitors selected from (3S,10aR)-6-X-2,3-dihydro-3-hydroxymethyl-2-methyl-10H-3,10a-epidithiopyrazino[1,2-a]indol-1,4-dion, wherein X may be hydrogen or a functional group selected from hydroxyl, cyanomethyloxyl, methoxy, ethoxy, acetoxy, propionyloxy or methoxycarbonylmethoxy, and the salts thereof. These aromatic gliotoxin derivatives have been claimed in EP 0926242 for the treatment of tumours. However, the synthesis of these compounds does not appear from this document. Even though at the time of filing EP 0926242 it had been assumed that these compounds were suitable for the general treatment of tumours, it has been shown that the plurality of tumours, or neoplasias, respectively, could not effectively be treated by gliotoxin and its derivatives (cf. i.a. FIGS. 7 and 8A), so that a general applicability of these sub-stances can by no means be assumed. The present invention now includes the use of gliotoxin and its Notch2-inhibiting derivatives for the preparation of a medicament for the treatment of special forms of tumours, i.e. of Notch2-associated tumours. The specific effect on a cellular target, i.e. abnormal Notch2$^{IC}$, is essential in active substances. The more indirectly a substance acts, the more relevant become its side effects, which may be quite considerable in case of gliotoxin. An activity at therapeutically relevant concentrations of 0.2 µM (~65 ng/ml unmodified gliotoxin) can be considered to be a reference value.

Therefore, it is particularly preferred according to the present invention that the Notch2-inhibitor is present at a therapeutical concentration of below 1 µM, preferably between 0.01 and 1 µM, more preferred, between 0.05 and 0.5 µM, and most preferred, at a concentration of 0.2 µM, especially less than 0.2 µM. The preferred serum concentration of 0.01 µM to 1 µM of gliotoxin after administration can accordingly be applied in doses. The active principle of gliotoxin, i.e. the rapid induction of apoptosis by execution of the activation induced cell death (AICD) suggests a single administration, or several administrations at one to three-week intervals, respectively. In special embodiments the dose above 0.1 mg per kg of the intended patient, preferably above 0.01 mg/kg, above 0.05 mg/kg or above 1 mg/kg. Most preferred the dose is below 30 mg/kg, below 20 mg/kg, below 10 mg/kg below 5 mg/kg, especially below 1 mg/kg.

The Notch2 associated tumours (tumours with ligand-independent Notch2 fragments) are preferably first diagnosed by testing for ligand-independent Notch2 fragments before treatment with the Notch2 inhibitors. Every cancer is an individual product of random mutations therefore each cancer varies and different oncogenes and tumour-suppressor genes might be responsible for the malignancy. However some markers (like the presence of ligand-independent Notch2 fragments) are common in specific tumour classes which allows a classification in uniform instances. The tumour treatment which is disclosed herein therefore comprises diagnosis of the ligand-independent Notch2 fragment in instances where the Notch2 relevance is not yet known. Such diagnostic means are common in the art and are also provided in the examples herein (e.g. of a sample, measured in vitro). Preferably the diagnostic method is a band shift assay.

The number of cancers suspected to be influenced by ligand-independent Notch2 fragments is steadily increasing. It was recently found that hepatoblastoma cells (Tomlinson et al., AACR Meeting Abstracts, 2006/4/1) and the osteosarkoma cell lines hu-OSB, OS187, LM7, but not the osteosarkoma cell lines COL and SAOS2, (Zhang et al., AACR Meeting Abstracts, Apr. 1, 2006), (embryonal) brain tumour or cerebellar neoplasia (Fan er al., Cancer res. 64: 7787 (2004)), medulloblastoma, meningioma (Cuevas et al., Cancer Res. 65 (12): 5070 (2005)), prostate cancer and myeloma have an increased Notch2 expression. These carcinomas can be targets for the medicament of the present invention. In a later publication it was found that both Notch2 and Notch2 ligands are upregulated in melanocytic "dysplastic" nevi and melanomas (Massi et al., Modern Pathology 19:246 (2006)).

According to a preferred embodiment of the present invention, the tumour is B-CLL. B-CLL constitutes of a uniform type of cancer with signal-independent Notch2 variants (N2$^{IC}$), and therefore it is a suitable target for a medicament according to the present invention. The efficacy against this type of cancer is extensively described in the figures and in the exemplary embodiments.

A major advantage of a Notch2-inhibitor for the treatment of B-CLL is the possibility of using the Notch2 target gene CD23 as a biomarker/tumour marker. CD23 is spontaneously cleaved from the cell surface and is easily detectable in patient sera as soluble CD23 (sCD23) by means of ELISA (Schwarzmeier et al., Leukemia & Lymphoma 46: 157; 2005). The sCD23 values correlate with the total tumour mass and therefore can be employed as tumour marker for therapy monitoring. By this monitoring, a therapy concentration of the Notch2 inhibitor can easily be adapted individually to the medicinal conditions of a patient.

Pancreas tumours are not as uniform as B-CLL. Approximately 50% are Notch2 associated. With the diagnostic method performed previous to therapy with the inventive medicament these 50% can be specifically treated.

Preferably, the present invention is used within the scope of the treatment of tumours which are selected from the group consisting of liver cancer (preferably hepatocellular carcinoma or hepatoblastoma) melanoma, marginal zone lymphoma, medulla-blastoma, bile duct carcinoma, pancreas carcinoma, pulmonary carcinoma and prostate carcinoma. Further tumours include osteosarkoma, cerebellar neoplasia, meningioma and myeloma. Notch2-associated, i.e. hepatocellular carcinoma characterised by ligand-independent Notch2 fragments, is given e.g. in cell line SNU398. For the treatment of non-Notch2-associated liver cancer, such as e.g., in the cell line Huh7, gliotoxin has too little or no effect. A merely slight effect would render gliotoxin useless as a pharmaceutical substance, because of its toxicity. Only a low effective concentration and a high therapeutic index (quotient of EC50 (effective dose) and LD50 (lethal dose) enable the use according to the present invention. The poor or lacking effect of gliotoxin in non-Notch2-associated cancer types shows that Notch2 inhibitors cannot be in general used for the treatment of cancer (e.g., all the liver carcinomas or leukaemias). With the present invention, using gliotoxin as an example of a Notch2 inhibitor, the proof of an effect is given, so that Notch2 inhibitors can specifically be used for an anti-tumour therapy. Thus, it has to be understood that the above-indicated tumour types exclusively relate to Notch2-associated tumour types. (Notch2-association in medulloblastoma: Fan et al., (Cancer Research 64: 7787, 2004); in melanomas: Hek et al. (Cancer Research 64: 5270, 2004); in pancreas carcinoma: Lee et al. (Lab. Invest., May, 2005, E-pub); in pulmonary carcinoma: Garnis et al. (Hum. Mol. Gen. 14: 475, 2004); in prostate carcinoma: Martin et al. (Cancer Research 64: 347; 2004) and Santagata et al. (Cancer Research 64: 6854; 2004)). Notch2-associated tumours (some cell lines of the hepatocellular carcinoma, pancreas carcinoma) are extremely sensitive to low gliotoxin doses, whereas in this dosage range no cytotoxic effect of these substances can be observed in the cell lines blind tested so far (e.g. HeLa, cervix carcinoma).

In this context, particularly preferred are tumours which form the basis of the clinical specifications (or clinical findings) of the cell lines SNU398 (hepatocellular carcinoma), MelJuso (malignant melanoma), Nec (cholangiocellular carcinoma) or Panc-1 (pancreatic carcinoma).

In particular, melanoma, especially characterised by the clinical specifications of the cell lines MelJuso and 518A2, is a preferred object of the present invention. These cell lines exhibits a Notch2 activity comparable to that of B-CLL (cf. FIG. 6B).

Also in these tumours, the Notch2 oncogene plays a central part in the immortalisation, in the differentiation arrest and in the apoptosis resistance. Data from cDNA microarray studies show that hepatocellular carcinomas, pancreas carcinomas and melanomas possibly over-express truncated Notch2-forms.

The proliferation signals which are more highly effective in these cells induce NR4A1 analogous to B-CLL, and thus intrinsically have established a pro-apoptotic program which is blocked via an intensified Notch2 activity. Moreover, these tumours often exhibit an increased expression of the anti-apoptotic protein BCL2 which, even though essential in the context of the NR4A1-induced apoptosis (Lin et al., Cell 116: 527; 2004), renders these tumour extremely resistant relative to conventional chemotherapies. In general, it can easily be determined by gene expression analysis whether or not a certain type of cancer is a Notch2-associated tumour which can be treated according to the invention. Notch2-associated tumours have an expression pattern which is comparable to the tumour examples herein described with regard to the Notch2 expression. Non-Notch2-associated tumours, with regard to their Notch2-expression pattern approximately correspond to HeLa or cervix carcinoma.

According to a further preferred embodiment of the present invention, the medicament comprises a pharmaceutical carrier. Pharmaceutical carrier substances serve for a better tolerance of the medicament and allow for a better solubility as well as a better bioavailability of the active substances contained in the medicament. Examples of this are emulsifiers, thickening agents, redox components, starch, alcohol solutions, polyethylene glycol or lipids. The choice of a suitable pharmaceutical carrier is highly dependent on the manner of administration. For oral administrations, liquid or solid carriers may be used, for injections, liquid final compositions are required.

Preferably, the medicament to be used according to the invention comprises buffer substances or tonic substances. By means of a buffer, the pH of the medicament can be adjusted to physiological conditions, and moreover, pH fluctuations can be attenuated, or buffered, respectively. An example thereof is a phosphate buffer. Tonic substances serve for adjusting the osmolarity and may comprise ionic substances, such as, e.g., inorganic salts, such as NaCl, or also non-ionic substances, such as, e.g., glycerol or carbohydrates.

Preferably, the medicament to be used according to the invention is prepared to be suitable for oral or intranasal administration. These administration forms of the medicament of the present invention allow for a rapid an uncomplicated uptake of the active substances via the mucous membranes. For a nasal intake, nose drops or nose sprays are suitable. For an oral administration, solid or liquid medicaments may, e.g., be taken directly or in a dissolved or diluted state, respectively.

The medicament to be used according to the invention preferably is prepared for an intravenous, intra-arterial, intramuscular, intravascular, intraperitoneal or subcutaneous administration. For this purpose, e.g., injections or transfusions are suitable. Administrations directly into the bloodstream have the advantage that the active substances of the medicament will be distributed in the entire body and will quickly reach the target tissue. In the case of B-CLL, the target-B cells mostly are to be found in the spleen and in peritoneal/pleural cavities, where they can quickly react to blood- and intestinal antigens.

A further embodiment provides for the use for preparing a medicament for topical application. Particularly melanomas could be treated by a local, topical application of such a medicament, e.g. as a patch, makes sense, wherein the active substance can be administered directly to the affected sites. Moreover, hepatocellular carcinomas could be treated locally by chemoembolisation with such a medicament. Furthermore such a medicament could be applied endoscopically for the treatment of cholangiocarcinomas.

A further aspect of the present invention resides in a method of treating tumours in patients, which tumours are characterised by ligand-independent Notch2-fragments (i.e. whose mechanism of action comprises an apoptosis inhibition, which has an etiological connection with ligand-independent Notch2 fragments), wherein a Notch2 inhibitor, preferably gliotoxin, is administered in an effective amount to a patient suffering from such a tumour. Such tumours may be present in a living being, preferably in a mammal, more preferably in humans, wherein a Notch2-inhibitor-containing (in particular, a gliotoxin-containing) medicament, which can be prepared as described above, is administered. Preferred administrations are oral, nasal, intravenous, intra-arterial, intramuscular, intravascular, intraperitoneal, topical or subcutaneous administrations.

The present invention will be further explained in more detail by the following Figures and Examples without, however, being restricted thereto.

FIGURES

FIG. 1: The role of NOTCH2 in binary B-cell fate decisions and its possible implication in the initiation of B-CLL. Early B-cell development takes place in the fetal liver (for B1 B-cells) and postnatal in the bone marrow (for B2 B-cells), respectively. Enforced expression of constitutive active N2$^{IC}$ promotes the selective development of CD5+ B1 B-cells while blocking the development of conventional B2 B-cells at the pre B-cell stage. In the spleen, Notch2 drives transitional B-cells into the marginal zone (MZ) B2 B-cell pool while blocking the differentiation of follicular B2 B-cells. Deregulation of Notch2 signaling might be implicated in the pathogenesis of B-CLL. Mutations leading to a Notch2 gain of function phenotype might take place in self-renewing B1 B-cells which could bear somatic hypermutations in their IgV gene regions or, alternatively, in early bone marrow B2-B-cell progenitors. SR: self renewing capacity.

Figure 2:
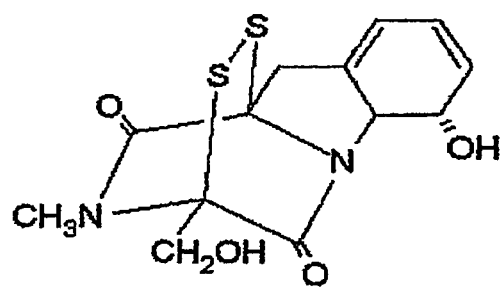

FIG. 2: Generic structure of Gliotoxin, an epidithiodioxopiperazine characterised by the presence of an internal disulphide bridge. Gliotoxin is a fungal toxin produced by *Aspergillus fumigatus, Trichoderma virens, Penicillium* spp., and *Candida albicans*. Molecular weight and structural formula of gliotoxin (2,3,5a,6-tetrahydro-6-hydroxy-3-(hydroxymethyl)-2-methyl-10H-3a,10a-epidithiopyrazino[1,2a]indole-1,4-dione), mol weight 326.4 Da, Formel: $C_{13}H_{14}N_2O_4S_2$.

Figure 3:
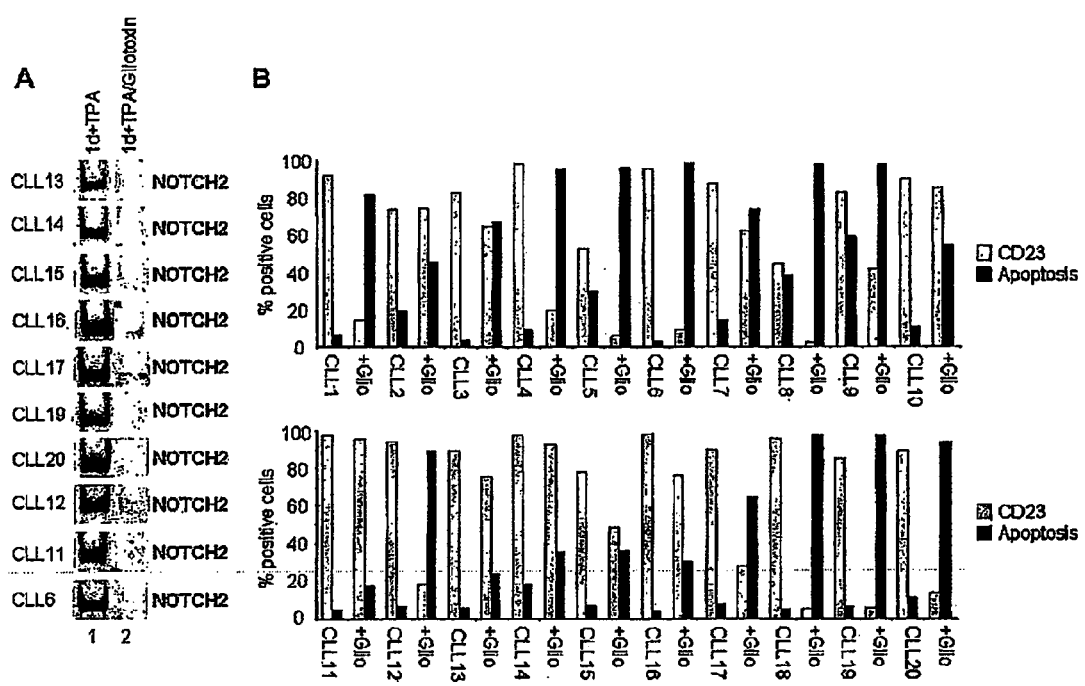

FIG. 3: Gliotoxin is a potent Notch2 trans-activation inhibitor in B-CLL cells. (A) EMSA showing the inhibition of DNA-bound Notch2IC complexes in the presence of 0.2 µg Gliotoxin. B-CLL samples (n=10) were cultured in the presence of 1 ng/ml TPA with or without 0.2 µM Gliotoxin for 24 hours. Nuclear extracts were subjected to EMSA using a oligonucleotide probe spanning a well defined CBF1/NotchIC binding site derived from the CD23a promoter. (B). Corresponding FACS analysis (plus 10 additional B-CLL samples) showing the downregulation of the Notch2 target gene CD23 as well as the induction of apoptosis of Gliotoxin treated B-CLL samples. Columnes represent the percentage of $CD19^+CD23^+$ (grey bars) and apoptotic cells (black bars: including early apoptotic cells single positive for AnnexinV, and late apoptotic cells double positive for AnnexinV and probidium iodide), respectively.

Figure 4:
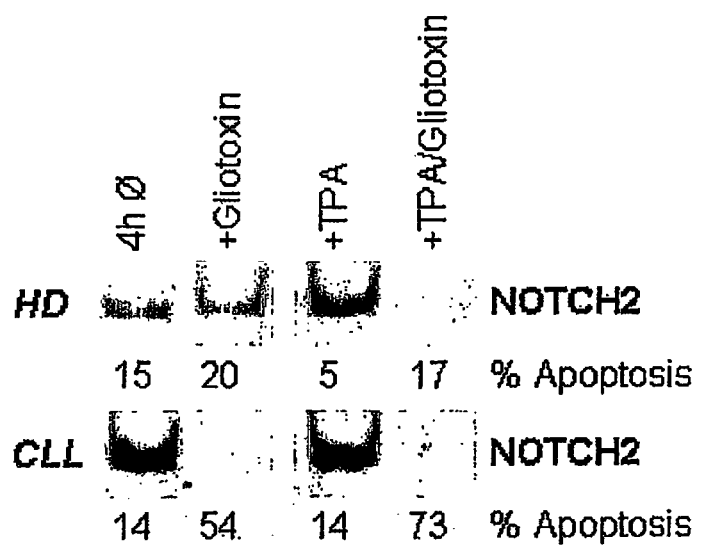

FIG. 4: Gliotoxin induces apoptosis in unstimulated as well as in TPA-stimulated B-CLL cells within 4 hours. Normal PBMCs (peripheral blood mononuclear cells) from healthy donors show a markedly lower Notch2 activity. Although gliotoxin inhibits Notch2 also in normal, TPA-stimulated cells, the gliotoxin-caused apoptosis rate is markedly lower in normal cells as compared to B-CLL cells. Non-stimulated and TPA stimulated PBMC's from healthy donors (HD) are less sensitive to 0.2 µM Gliotoxin despite a basal Notch2 activity. PBMC's and CLL cells were incubated with 0.2 µM Gliotoxin with or without TPA for 4 hours and the Notch2 activity as well as the percentage of apoptotic cells were determined by EMSA and FACS analysis, respectively.

Figure 5:
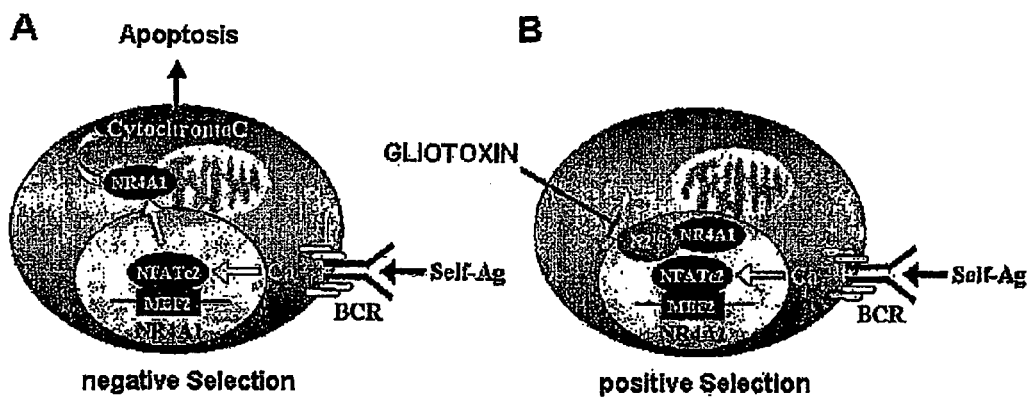

FIG. 5: A model for the apoptotic effect of Gliotoxin in B-CLL cells. (A) Stimulation through the B-cell receptor (BCR) induces NF-AT signaling which in turn activates expression of the orphan steroid receptor NR4A1. Without Notch2 signaling, NR4A1 translocates to the cytosol where it interacts as pro-apoptotic factor with Mitochondria leading to apoptosis by cytochrome C release (a mechanism known as activation induced cell death; AICD). (B) In the presence of activated $N2^{IC}$ (B-CLL), NR4A1 is retained in the nucleus through direct interaction with nuclear $N2^{IC}$. This mechanism regulates the homeostasis of $CD5^+B1$ B-cells and is found in secondary lymphoid tissues where Notch2 expressing B1 B-cells are stimulated by Notch2 ligands expressed on neighboring cells (or in B-CLL cells where Notch2 is deregulated). Gliotoxin inhibits the activity of Notch2 thereby releasing B1 B-cells (or B-CLL cells) from their anti-apoptotic state.

Figure 6:
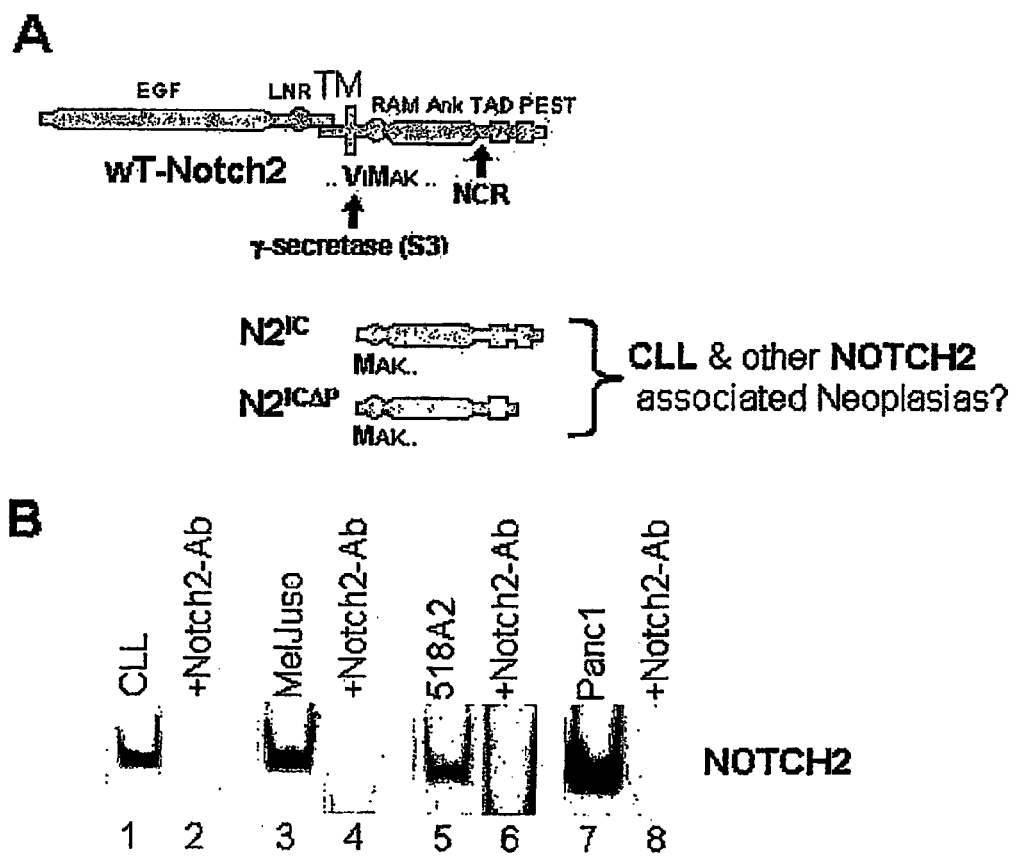

FIG. 6: Structural features of oncogenic Notch2 forms. (A) Ligand induced wT-Notch2 signaling is dependent on γ-secretase mediated cleavage on a conserved valin (S3 site) proximal to the transmembrane domain. The lower part of FIG. 6A indicates truncated, γ-secretase independent Notch2 forms ($N2^{IC}$ and $N2^{IC\Delta PRST}$) which might be expressed in B-CLL cells and in other Notch2 associated neoplasias like melanom and pancreas carcinomae. EGF: Epidermal Growth Factor like repeats; NLR: cysteine rich Lin-1/Notch repeats; TM: transmembrane domain; RAM: CSL binding domain; Ank: ankyrin/CDC10 repeats; TAD: transactivation domain; PEST: protein degradation signal. (B) EMSA showing that the melanoma cell lines MelJuso and 518A2 as well as the pancreas carcinoma cell line Panc1 express constitutive active forms of Notch2. Lane 2, 4, 6, and 8 show supershift assays including antibodies specific for Notch2IC.

FIG. 7: (A) The apoptotic activity of gliotoxin on further B-CLL patient samples (CLL4-CLL8) is illustrated. The (non-Notch2-associated) leukaemia cell lines (or the leukaemia cell lines not characterised by ligand-independent Notch2 fragments) Jurkat (T-ALL), SH1 (hairy cell carcinoma), RL-7 and K562 (CML) are resistant to a treatment with 0.2 µM (corresponding to 60 ng/ml) of gliotoxin. Cells were incubated for 24 h+/−gliotoxin, and the percentage of apoptotic cells (probidium-iodide+/annexinV+) was determined by means of FACS analysis. In none of the 4 non-Notch2-associated cell lines indicated, the application of 0.2 µM of gliotoxin led to a significant induction of apoptosis within 24 hours. The cytotoxic effect of Gliotoxin correlates with the Notch2 activity in leukemias. (B) Corresponding EMSA showing the activity of Notch2 in B-CLL cells and in leukemic cell lines (Jurkat, SH1, RL7, and K562).

Figure 8:
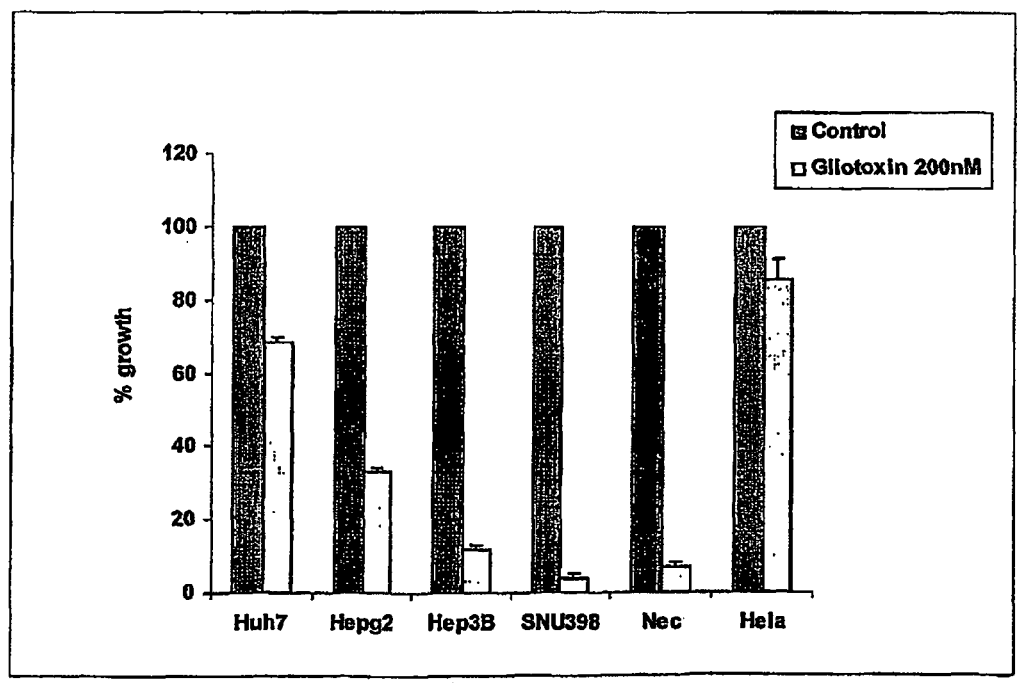
Figure 8:
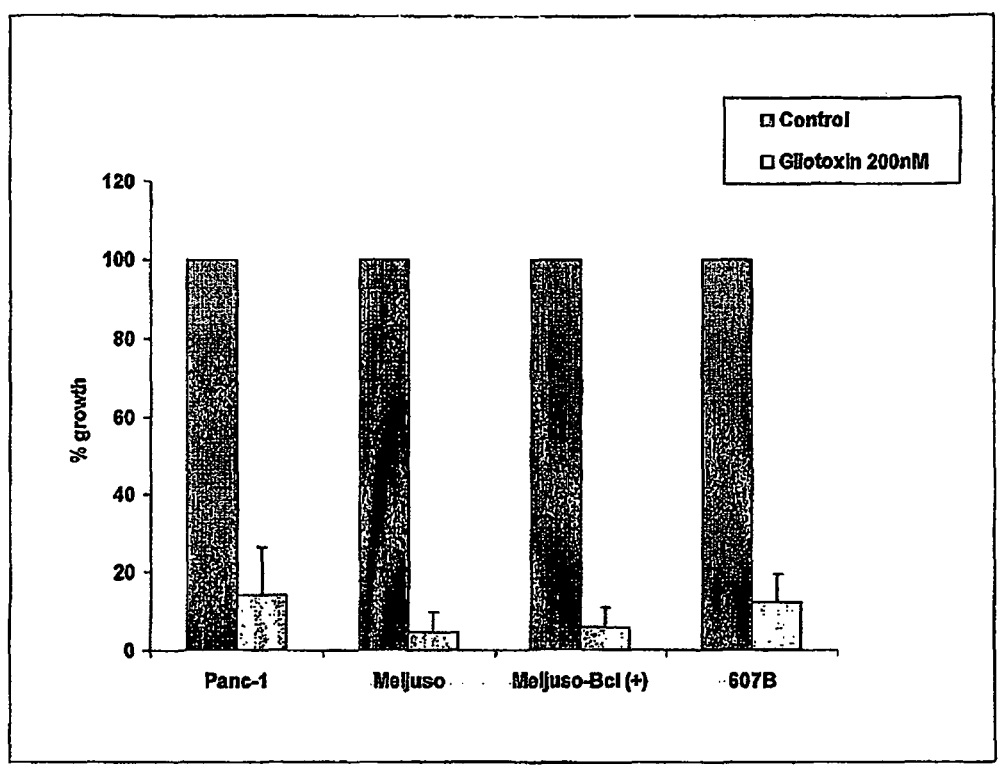
Figure 8:
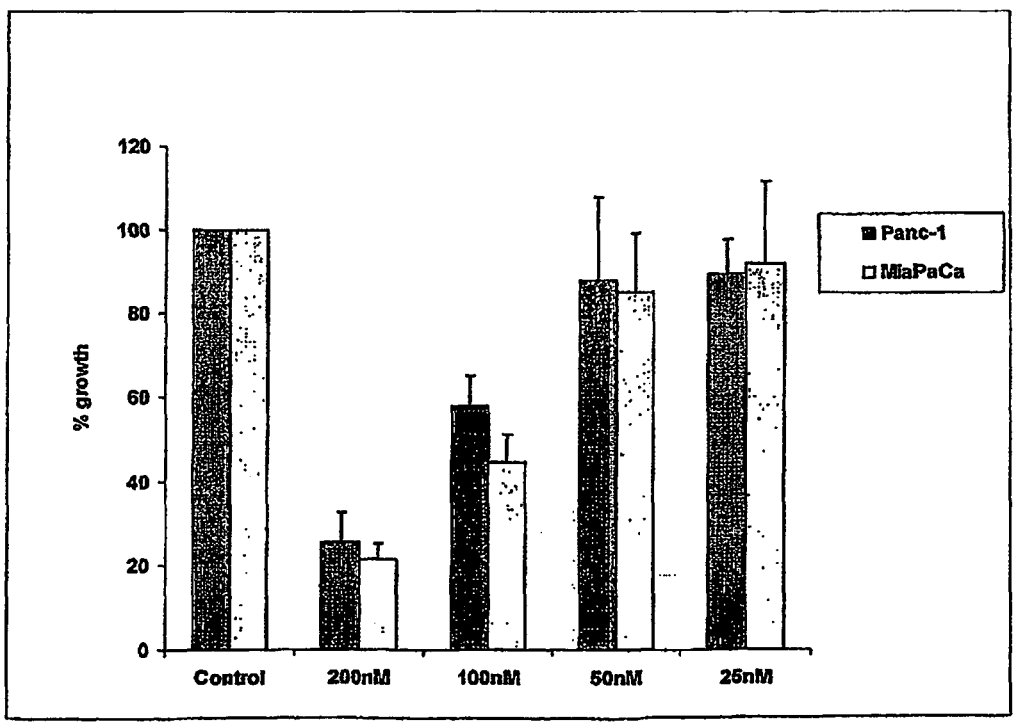
Figure 8:
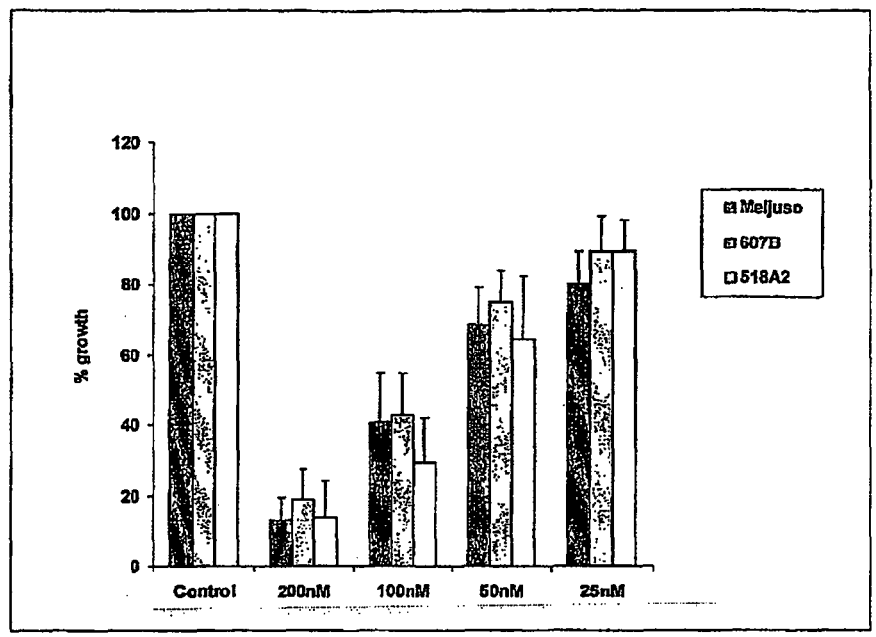

FIG. 8 *a-d*: Effects of gliotoxin on cell counts of various human tumour cell lines in vitro. Cell counts of a) hepatocellular carcinoma cell lines HepG2, Huh7, SNU398, Hep3b, HeLa (cervix) and the cholangiocarcinoma cell line NEC as well as b) the pancreatic cancer cell line Panc-1 and the melanoma cell lines d) MelJuso, Meljuso-Bcl-2 (+) and 607B after 72 h treatment with 200 nM gliotoxin; c-d) Cell count dose range experiments with c) pancreatic carcinoma cell lines Panc-1 and MiaPaCa as well as melanoma cell lines MelJuso, 518A2 and 607B using 25, 50 100 and 200 nM gliotoxin for 24 h. All data are given relative to control ±standard deviation.

Figure 9:
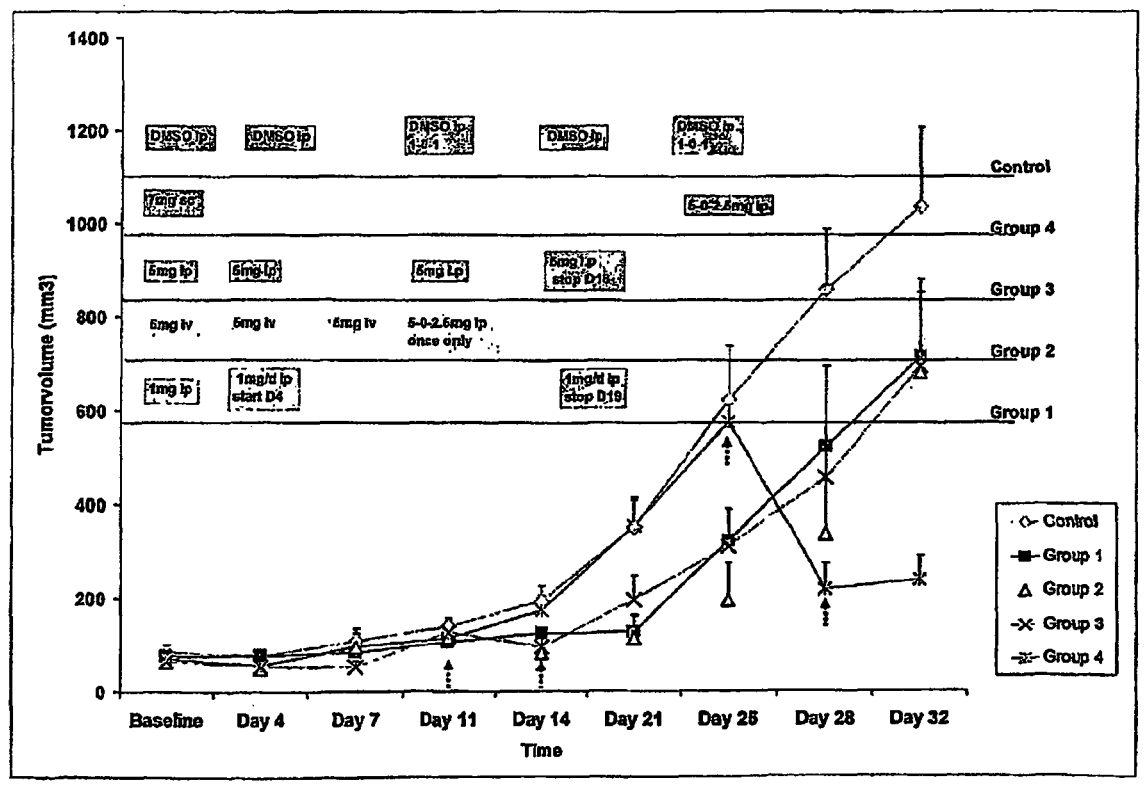

FIG. 9: Effects of gliotoxin in a 518A2 melanoma nude mouse xenograft model. 518 A2 cells ($9 \times 10^6$) were inoculated into the lower right and left flank of each mouse. Six days after implantation, tumours had a mean volume of 75 mm³ and mice were randomized into 4 treatment groups (n=6/group) and 1 Control group (n=8). The flexible dose and treatment schedule of each group are given in the squares next to each group in the figure. All data are given as mean tumour volumes ±95% CI. The dotted arrows indicate a significant decrease of tumour volume (Wilcoxon matched pairs test, P<0.05) within Group 2 and Group 4 three days after application of 5 mg-0-2.5 mg of gliotoxin. It was shown that even at late administrations with progressed tumours gliotoxin administration is effective group 4 (ip administration at day 25).

Figure 10:
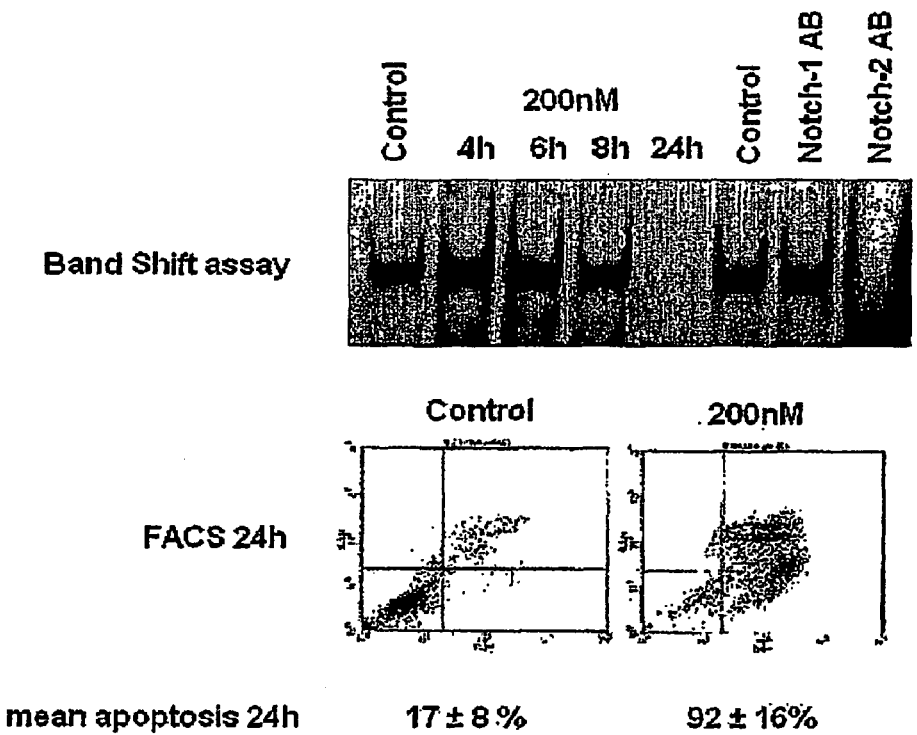
Figure 10:
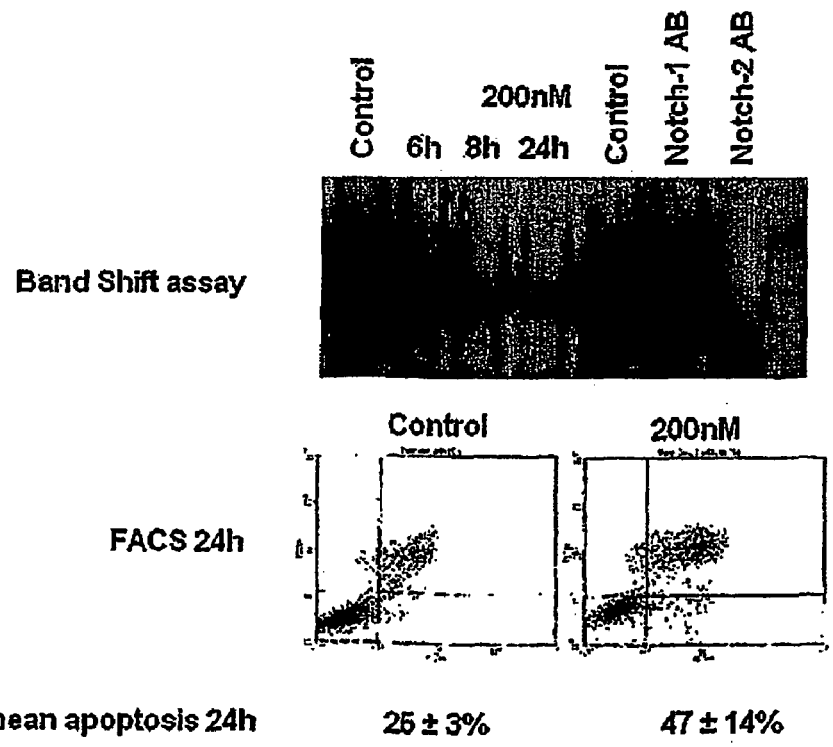

FIG. 10 *a-b*: Effects of gliotoxin on Notch2 regulation and apoptosis. The melanoma cell line 518A2 (A) and the pancreatic cancer cell line Panc-1 (B) were treated with 200 nM gliotoxin or vehicle control for 24 h Notch2 activity was analysed by band shift assay. Apoptosis was measured as annexin V and 7-AAD double positivity by FACS. Data are given as percentage of apoptotic cells ±standard deviation. Whereas almost all cells of the 518A2 cell line (melanoma) could be found in apoptosis (92%) the apoprosis rate of Panc-1 was significantly lower (47%, control 25%). The lower efficacy of 200 nM gliotoxin in Panc-1 cells is reflected by band shift assay where the extremely high Notch2 activity in this cell line could be only partly inhibited by the drug concentration used.

EXAMPLES

As drug screening model, a cell culture system was established which conserves the phenotype of freshly isolated B-CLL cells (3×10⁶ B-CLL cells/ml RPMI medium+10% FCS, supplemented with 1 ng/ml of TPA). Notch2 activity in the cell nucleus is determined by means of EMSA (electrophoretic mobility shift assay) experiments, and the cell viability (Probidium iodide/annexinV) and CD23 expression (Notch2 target gene) is determined by means of FACS (flow cytometry) analyses, respectively.

Example 1

Cell Lines and Material

Human cell line SNU-398 (ATCC Nr. CRL-2233, Park, J. G. et al., *Int. J. Cancer* 62, 276-282 (1995)) corresponds to the clinical image of a trabecular anaplastic hepatocellular carcinoma and originates from a 42 year old male asiatic patient with chronic Hepatitis B.

Human cell line HepG2 (ATCC Nr. HB-8065, Knowles et al. *Science* 209, 497-499 (1980)) corresponds to the clinical image of a hepatocellular carcinoma and originates from a 15 year old male white patient.

Human cell line Hep3B (ATCC Nr. HB-8064) corresponds to the clinical image of a Hepatitis B-conditioned juvenile hepatocellular carcinoma and originates form a 8 year old male black patient.

Human cell line Huh-7 also originates form a patient with hepatocellular carcinoma (Sato, Y. et al., *Gut* (2006)) and was kindly provided by Markus Peck-Radosavljevic (Medical University of Vienna, Austria).

Human cell line Nec originates from a patient with cholangiocellular carcinoma and was kindly provided by Munechika Enjoji (Kyushu University, Fukuoka, Japan).

Human pancreas carcinoma cell line Panc-1 (ATCC Nr. CRL-1469, Lieber et al., *Int. J. Cancer* 15, 741-747 (1975)) and MiaPaCa (ATCC Nr. CRL-1420, Yunis et al., *Int. J. Cancer* 19, 128-135 (1977)) are cell lines directly isolated from two patients with pancreas carcinoma.

Human melanoma cell lines 518A2 and 607B were described by Jansen et al. (*Nat. Med* 4, 232-234 (1998)) and kindly provided by Peter Schrier, (University Leiden, Netherlands).

Human melanoma cell line MelJuso (Lehmann et al., *Proc. Natl. Acad. Sci. U.S.A* 86, 9891-9895 (1989)) originates from a patient with a malignant melanoma and was kindly provided by Judith Johnson (University Munich, Germany). The Bcl-2 over expressing cell line was kindly provided by Barbara Pratscher (Medical University of Vienna, Austria).

All cell lines were amplified in standard cell culture medium (RPMI or DMEM, Gibco BRL, Paisley, Scotland) cultivated with 10% fetal calf serum and 1% antibiotic antimycotic mixture at 5% C02 and 95% air moisture at 37° C.

Gliotoxin was obtained from FLUKA (Sigma Aldrich, Seelze, Germany). For in vitro studies a 1 μM gliotoxin stock solution was prepared with 98% alcohol and further diluted to concentrations as indicated. For animal studies respective gliotoxin concentrations were prepared in a 2% DMSO solution.

Example 2

Methods

Cell Count Analysis

Tumour cells were seeded at a density of 10,000 cells/well in 24-well plates. 24 h after seeding, medium containing gliotoxin was added to yield desired concentrations of gliotoxin. At time points indicated, culture medium was removed by suction. Adherent cells were washed with DPBS (Cambrex, Verviers, Belgium) and incubated with trypsin (Gibco) at 37° C. Detached cells were transferred to test tubes containing Cellpack isotonic fluid (Sysmex Europe, Bornbarch, Germany) and counted with a Coulter Z1 electronic cell counter (Beckman Coulter, Bedford, UK).

Flow Cytometry

Tumour cells were seeded at a density of 50,000 cells/well in 6 well plates. 24 h after seeding, medium containing gliotoxin was added to yield desired concentrations of gliotoxin. After further 24 h cells were harvested, counted and washed twice with PBS. Then, 100,000 cells were resuspended in 100 μl binding buffer and stained with Annexin V-PE and 7-AAD (both Becton Dickinson, N.J., USA) according to manufacturer's recommendations. After 20 minutes incubation time at room temperature in the dark, 400 μl binding buffer was added and immediately analyzed on a FACScalibur flow cytometer using CellQuest software (both Becton Dickinson, N.J., USA)

Band Shift Assay: Effect of Gliotoxin on B-CLL Notch2 Activity

B-CLL cells were cultured for 24 h in the presence of 0.2 μM/ml of gliotoxin. This treatment led to a dramatic loss of the transcriptional Notch2 activity, as shown in the following representative EMSA (FIG. 3). Since the Notch2 activity in B-CLL cells correlates with the cell viability thereof, the loss of the nuclear Notch2 did not only lead to the loss of the CD23 expression, but also to a massive induction of apoptosis (n=10; mean value of apoptosis: 73%). FIG. 3 shows several representative gliotoxin-sensitive B-CLL cases.

To demonstrate the specificity of the Notch2-inhibiting effect of gliotoxin, B-CLL cells as well as control-PBMCs from healthy donors (within 4 hours, also normal recirculating lymphocytes show a certain residual Notch2 activity) were treated for a short period of time (4 hours) with 0.2 μM of gliotoxin, where the Notch2-inhibiting function of gliotoxin was confirmed. After 4 hours of gliotoxin treatment, massive signs of the starting apoptosis (AnnexinV+) could already be recognized in B-CLL cells. This effect was increased by TPA (a phorbol ester which stimulates the activation of lymphocytes).

In the control, a marked reduction of the physiologic Notch2 activity by gliotoxin only appeared in TPA-stimulated PBMCs. In comparison to B-CLL cells, normal PBMCs are far less sensitive to the pro-apoptotic effect of gliotoxin (non-stimulated: 20% apoptosis in PBMCs versus 54% in B-CLL cells; TPA-stimulated: 17% apoptosis in PBMCs versus 73% in B-CLL cells.

Band Shift Assay: Effect of Gliotoxin in Further Notch2-Associated Neoplasias 500,000 cells were seeded on 12 cm² plates for 24 h and then treated with 200 nM gliotoxin. At the time points as indicated cells were harvested and immediately frozen at −80° C. The band shift assay was performed as described for B-CLL.

A screening for the efficacy of gliotoxin in cell lines of hepatocellular carcinomas, melanomas and pancreas carcinomas showed that gliotoxin massively induces the apoptosis in certain cell lines. In FIGS. 7 and 8, a representative screening can be seen, where the cell lines indicated (Jurkat (T-ALL), SH1 (hairy cell carcinoma), RL-7 and K562 (CML), hepatocellular carcinoma cell lines: Huh7, Hepg2, Hep3B, SNU398; bile duct carcinoma: Nec; pancreas carcinoma cell line: Panc-1; melanoma lines: MelJuso-wT. MelJuso+BCL2 transduced) were cultured for 72 hours in the presence of 0.2 μM gliotoxin and subsequently the amount of cells was determined (×10³ cell count). Gliotoxin proved particularly effective in the hepatocellular cell lines SNU398 and in the bile duct carcinoma cell line Nec, as well as in the pancreas carcinoma cell line Panc-1. Particularly striking was the effect in melanoma cell lines which are considered to be particularly resistant to conventional forms of therapy. Even an over-expression of the anti-apoptotic protein BCL2 in the melanoma cell line MelJuso showed only a slight protective effect against a gliotoxin treatment. This phenomenon can probably be explained by the fact that in the course of the AICD, BCL2 becomes an inducer of apoptosis via an interaction with TR3 (NR4A1) by a conformational change.

Tumour Xenograft Model

Pathogen-free, 4-6 week old, female athymic nude mice (Harlan Winkelmann, Borchen, Germany) were housed under sterile conditions and treated according to the regulations of the local animal welfare committee. Hundred µl of a tumour cell suspension in DPBS containing $9 \times 10^6$ 518A2 cells were inoculated into the lower right and left flank of each mouse. When mean tumour volume reached approximately 75 mm³ (based on caliper measurements), mice (n=8/control group, n=6/treatment group) were randomly assigned to treatment groups and received one of the following treatment regimens:

Control (2% DMSO), Group 1 (start dose 1 mg/kg i.p.), Group 2 (start dose 5 mg/kg i.v.), and Group 3 (start dose 5 mg ip) and Group 4 (start dose 7 mg s.c.).

Flexible explorative dosing schedule was used in this in vivo trial: At baseline, all treatment groups received their respective start dose to estimate immediate toxicity of gliotoxin. Beginning with day 4:

Group 1 received 1 mg/kg daily including day 19.

Group 2 received 5 mg i.v. at day 4 and day 7 followed by 5 mg-0-2.5 mg ip at day 11

Group 3 received 5 mg/kg i.p. once weakly including day 18.

Group 4 suffered severe local toxicity after subcutaneous application of the 7 mg/kg start dose, so subcutaneous treatment was not repeated. Group 4 remained untreated until day 25 and received then 5 mg-0-2.5 mg once only. The trial was stopped when control mice reached a mean tumour volume of 1000 mm³.

Statistics

Cell count data are given as mean relative of respective controls experiments ±standard deviation. FACS data are given as mean percentage of Annexin V and 7-AAD double positive cells ±standard deviation.

In the xenograft melanoma model, tumour volume of each group is given as mean±95% confidence interval. The antitumour effect of gliotoxin was described as tumour volume of treatment group/tumour volume of control group×100 (T/C).

Statistical significance of differences among treatment groups was calculated by using one-way ANOVA and Bonferroni's test was used for post-hoc comparisons using SPSS software (SPSS 10.0.7, SPSS Inc., Chicago, Ill.). Differences in mean tumour volume between two time points within treatment groups were calculated by using the Wilcoxon matched pairs test. P-values less than 0.05 were considered to be of statistical significance.

Example 3

Gliotoxin is Active Against Various Solid Tumour Cells In Vitro

In a first screen we tested the activity of gliotoxin against hepatocellular carcinoma HCC, cholangiocellular carcinoma (CCC); pancreatic carcinoma and melanoma cells in vitro.

In B-CLL, first a concentration of 200 nM gliotoxin was used. Treatment of HCC cell lines Huh7, HepG2, Hep3B, SNU398, the CCC cell line Nec with 200 nM gliotoxin for 72 h resulted in a mean reduction of cell numbers by 31% (Huh7), 67% (HepG2), 88% (Hep3B), 96% (SNU398) and 93% (Nec) compared to vehicle treated controls (FIG. 8a). Remarkably, gliotoxin was very effective in the cell lines Panc-1, Meljuso-wt, the Bcl-2 over expressing Meljuso-Bcl-2 (+), 607B and 518A2, representing pancreas carcinoma and melanoma, which are tumours known to be very resistant to other therapies (FIG. 8b). Even the Bcl-2 over expressing melanoma cell line Meljuso-Bcl-2 (+) showed a cell count decrease by 94% after 72 h of gliotoxin treatment (FIG. 8b). Thus, melanoma and pancreatic carcinoma were used as representative gliotoxin sensitive tumours for further evaluation.

Next, it was tested whether lower doses of gliotoxin could reveal similar effects observed with 200 nM. Dose range experiments with Panc-1 and MiaPaCa as well as Meljuso, 607B and 518A2 (FIG. 8c-d) using 25, 50, 100 and 200 nM for 24 h revealed a clear dose dependent cytotoxicity of gliotoxin compared to vehicle treated control. However, in line with the results observed for B-CLL, a gliotoxin concentration as low as 200 nM turned out to be the most effective dose (P<0.001 for all cell lines) and was chosen for subsequent analysis of notch-2 activity by band shift assay and quantification of apoptosis by flow cytometry.

In line with the data derived from B-CLL, 518A2 (FIG. 10a) and particularly Panc-1 (FIG. 10b) showed a strong baseline activity of notch-2. Incubation with 200 nM gliotoxin resulted in a time dependent down regulation of Notch-2 activity reaching its maximum 24 h after beginning of treatment. Extent of apoptosis correlated well with the degree of Notch-2 downregulation leading to 92% (518A2, P<0.05) and 47% (Panc-1, P<0.05) apoptotic cells.

Example 4

Truncated Notch2-Forms in B-CLL

Gene aberrations (Nickoloff et al., supra; Radke et al., supra) may lead to the expression of a truncated, ligand-independent $N^{IC}$ protein. Such neoplastic Notch-forms either can be activated constitutively by the γ-secretase on a conserved valine in the vicinity of the transmembrane domain (S3, FIG. 6A), or they are γ-secretase-independent by translation of a truncated Notch2 protein by initiation downstream of the S3 site. By incubation of B-CLL cell cultures with 50 nM Dapt, a γ-secretase inhibitor ($IC_{50}$=5-10 nM) and inhibitor of the ligand-dependent Notch2 signal, it was proven that the high $N2^{IC}$ activity of freshly isolated peripheral B-CLL-lymphocytes and in TPA (12-O-tetradecanoylphorbol-13-acetate)-treated B-CLL-suspension cell cultures is a result of the expression of a ligand-independent Notch2. Dapt had no influence on the activity of $N2^{IC}$. By this, it can be concluded that B-CLL cells express a truncated Notch2 which does not have a transmembrane domain.

In particular, $N2^{IC}$ blocks the apoptotic function of the steroid receptor NR4A1, which belongs to the immediately near genes which are induced by apoptotic BCR-signals (AICD). Interestingly, in B-CLL cells the NR4A1-expression is highly increased, suggesting that these leukaemia cells have been programmed for apoptosis. However, due to the aberrant Notch2 signal, these cells are not capable of negative selection.

Example 5

Effect on Non-Notch2-Associated Cancer Types

In EP 926 241 A1, in Table I thereof, in 7 cell lines the effect of gliotoxin is shown by way of the $IC_{50}$-values (ng/ml) with regard to cell viability. In these cell lines, only in U937 (macrophage cell line; $IC_{50}$: 14); HCT-15 ($IC_{50}$: 39) as well as in mouse cell line P388 ($IC_{50}$: 5,8) an efficacy comparable to the present data was shown (0.2 µM corresponds to 60 ng/ml: here a almost 100% response is found in B-CLL-cases and in the cell lines SNU-398, Panc-1 and MelJuso+/−BCL2). In the melanoma cell lines MelJuso, in which gliotoxin proved to be particularly effective, a Notch2 activity comparable to that of B-CLL has been found (FIG. 6B).

Among further controls in which gliotoxin has not shown any effect are leukaemias (as control cell lines, Jurkat (T-ALL) K562 (CML), RL7 and SH1 (hairy cell leukaemia) have been tested (FIGS. 7 and 8A)) and solid tumours (0.2 µM gliotoxin has no significant effect on the cell count of HeLa cells (cervix carcinoma) within 72 hours). Further examples are indicated above (hepatocellular carcinoma of the cell lines Huh7, Hepg2, Hep3B).

In blind tests, in none of the leukaemia cell lines an effect of gliotoxin comparable to that of BCLL has been shown. In solid tumours, the trend is in a similar direction: MelJuso (melanoma), where Notch2 has been shown to be involved (FIG. 6B and Hoek et al., Cancer Research 64: 5270; 2004). Some cell lines of the hepatocellular carcinoma, of the bile duct carcinoma and of the pancreas carcinoma are extremely sensitive to low gliotoxin-doses, whereas in this dosage range no cytotoxic effect of this substance can be observed in the cell lines blind tested so far (e.g., HeLa, cervix carcinoma).

Example 6

Gliotoxin is Active in a Melanoma Nude Mouse Xenograft Model

Based on the results described above an in vivo pilot trial using a nude mice melanoma (518A2) xenograft model was performed (FIG. 9).

Beginning with day 14, Group 1 (1 mg/kg daily until day 19) Group 2 (3×5 mg iv within 7 days then 1×5 mg-0-2.5 mg) and Group 3 (5 mg/kg weekly until day 18) showed a significant difference in tumour volume compared to vehicle treated control (day 14: Control vs. Group 1: P=0.005, Group 2: Control vs. Group 2: P=0.00003) which remained significant until end of study. The greatest anti-tumour activity in Group 1, Group 2 and Group 3 was seen at day 21 (T/C: 37%, 32% and 49% respectively; P<0.001 for all groups vs. Control). Interestingly, detailed analysis of Group 2 revealed a significant decrease of mean tumour volume after application of 5 mg-0-2.5 mg between day 11 and day 14 (day 11 vs. day 15: 115 mm$^3$ vs. 83 mm$^3$, P=0.008).

Group 4 suffered local toxicity after s.c. application of 7 mg/kg gliotoxin, so treatment remained stopped until day 25. At day 25, the tumour volume of Group 4 did not differ significantly from Control (T/C: 92%, Group 4 vs. Control: P=1). Thus Group 4 was used as a late stage tumour model and applied 5 mg-0-2.5 mg, a dose schedule significantly decreasing tumour volume between day 11 and day 14 in Group 2.

Crucially this application at day 25 caused a significant decrease of mean tumour volume within Group 4 between day 25 and day 28 (Group 4: day 25 vs. day 28: 576 mm$^3$ vs. 218 mm$^3$, P=0.005). The greatest anti-tumour effect in Group 4 was seen at day 32 compared to Control (T/C: 23%, Control vs. Group 4: P=0.0002).

Based on these data it was concluded that gliotoxin is highly active in an early and late stage melanoma xenograft model.

The invention claimed is:

1. A method for the treatment of a cancer having ligand-independent Notch2 fragments comprising:
   diagnosing a cancer as a cancer having ligand-independent Notch2 fragments based on the detection of ligand-independent Notch2 fragments in the cancer;
   obtaining a gliotoxin or gliotoxin derivative; and
   administering an effective amount of the gliotoxin or gliotoxin derivative to a subject having the cancer having ligand-independent Notch2 fragments;
   wherein the cancer having ligand-independent Notch2 fragments is treated.

2. The method of claim 1, wherein the subject is a human.

3. The method of claim 1, wherein the gliotoxin derivative is acetylgliotoxin, 6-$C_{1-3}$-alkoxygliotoxin, 6-$C_{2-3}$-acyloxy-gliotoxin, 6-dihydro-gliotoxin, 6-dihydroxy-gliotoxin, 6-[(methoxycarbonyl)methoxy]-gliotoxin or 6-cyanomethoxy-gliotoxin, or a salt thereof.

4. The method of claim 1, wherein the gliotoxin derivative is a (3S,10aR)-6-X-2,3-dihydro-3-hydroxymethyl-2-methyl-10H-3,10a-epidithiopyrazino[1,2-a]indol-1,4-dione,
wherein X may be hydrogen or a functional group selected from hydroxyl, cyanomethyloxyl, methoxy, ethoxy, acetoxy, propionyloxy or methoxycarbonyl-methoxy, or a salt thereof.

5. The method of claim 1, wherein the gliotoxin or gliotoxin derivative is present in the subject at a serum concentration of below 1 µM after administration.

6. The method of claim 5, wherein the gliotoxin or gliotoxin derivative is present in the subject at a serum concentration of between 0.01 and 1 µM after administration.

7. The method of claim 1, wherein detecting the ligand-independent Notch2 fragments comprises performing a band-shift assay.

8. The method of claim 1, wherein the cancer is a B-cell chronic lymphocytic leukemia (B-CLL).

9. The method of claim 1, wherein the cancer is a melanoma, medulla-blastoma, bile duct carcinoma, pancreas carcinoma, pulmonary carcinoma, prostate carcinoma, cerebellar neoplasia, marginal zone lymphoma, osteosarkoma, cholangiocellular carcinoma, cerebellar neoplasia, meningioma, myeloma, or liver cancer.

10. The method of claim 9, wherein the cancer is a hepatocellular carcinoma or hepatoblastoma.

11. The method of claim 9, wherein the cancers are based on the clinical specifications of the cell lines SNU398 (hepatocellular carcinoma), MelJuso (malign melanoma), Nec (cholangiocellular carcinoma) and/or Panc-1 (pancreas carcinoma).

12. The method of claim 1, wherein the gliotoxin or gliotoxin derivative is comprised in a pharmaceutical carrier.

13. The method of claim 12, wherein the carrier comprises buffers or tonic substances.

14. The method of claim 1, wherein administering the gliotoxin or gliotoxin derivative comprises oral or intranasal administration.

15. The method of claim 1, wherein administering the gliotoxin or gliotoxin derivative comprises intravenous, intraarterial, intramuscular, intravascular, intraperitoneal, or subcutaneous administration.

16. The method of claim 1, wherein administering the gliotoxin or gliotoxin derivative comprises topical administration.

17. The method of claim 16, wherein the administration is via a topical patch.

* * * * *